United States Patent [19]

Daneshvar

[11] Patent Number: 5,460,606
[45] Date of Patent: Oct. 24, 1995

[54] URINARY CATHETERS, AND SUPPORT SYSTEMS THEREFOR

[76] Inventor: Yousef Daneshvar, 21459 Woodfarm, Northville, Mich. 48167

[21] Appl. No.: 982,634

[22] Filed: Dec. 28, 1992

[51] Int. Cl.[6] .................................................. A61M 29/00
[52] U.S. Cl. ........................... 604/96; 604/174; 604/179; 604/323; 604/326
[58] Field of Search .................. 604/96, 174, 178–180, 604/283, 322–323, 326, 349, 350, 361; 128/DIG. 26

[56] References Cited

U.S. PATENT DOCUMENTS

| | | | |
|---|---|---|---|
| 1,032,611 | 7/1912 | Keyes | 604/178 |
| 2,046,094 | 6/1936 | Schmidt | 604/179 |
| 2,213,210 | 9/1940 | Egbert | 604/179 |
| 4,089,337 | 5/1978 | Kronner | 604/178 X |
| 4,116,227 | 9/1978 | Eisenberg et al. | 128/2 |
| 4,416,664 | 11/1983 | Womack | 604/174 |
| 4,449,971 | 5/1984 | Cawood | 604/54 |
| 4,483,688 | 11/1984 | Akiyama | 604/265 |
| 4,561,857 | 12/1985 | Sacks | 604/174 |
| 4,615,692 | 10/1986 | Giacalone et al. | 604/94 |
| 4,810,247 | 3/1989 | Glassman | 604/171 |
| 4,846,816 | 7/1989 | Manfredi | 604/323 |
| 4,874,387 | 10/1989 | Boone | 604/326 |
| 4,878,901 | 11/1989 | Sachse | 604/174 |
| 4,888,005 | 12/1989 | Dingeman et al. | 604/326 |
| 4,976,698 | 12/1990 | Stokley | 604/174 |
| 5,100,396 | 3/1992 | Zamierowski | 604/305 |
| 5,114,398 | 5/1992 | Trick et al. | 600/29 |
| 5,190,530 | 3/1993 | Greeff et al. | 604/179 |
| 5,211,642 | 5/1993 | Clendenning | 604/410 |
| 5,236,422 | 8/1993 | Eplett, Jr. | 604/256 |
| 5,242,398 | 9/1993 | Knoll et al. | 604/101 |
| 5,304,145 | 4/1994 | Blair | 604/179 |

*Primary Examiner*—Corrine Maglione

[57] ABSTRACT

A support system for a Foley catheter attaches to a patient by abdomen and thigh straps and has a compartment that encloses a limited length of the catheter where the catheter exits the urethra. One purpose is to reduce the risk that a confused patient will cause self-injury by pulling the catheter out of the bladder. One embodiment of catheter has a disconnect feature that causes the inserted part of the catheter to remain in the bladder if the patient is able to grasp and pull a portion of the catheter that extends beyond the compartment. This feature also allows voluntary separation permitting a patient to move around temporarily without carrying a urine collection bag. The inserted part has a valve that may be either a check valve or a three-way stopcock. Another feature is an alarm system that gives an alarm if a patients attempts to pull the catheter out.

21 Claims, 12 Drawing Sheets

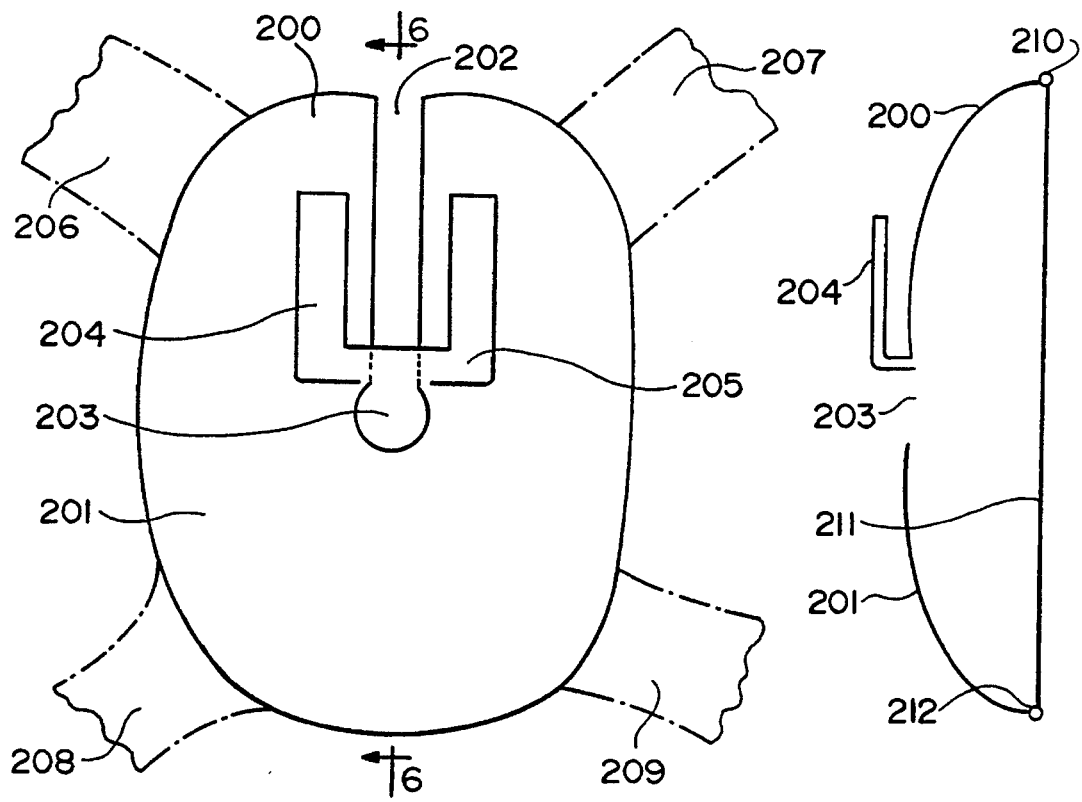
FIG. 5
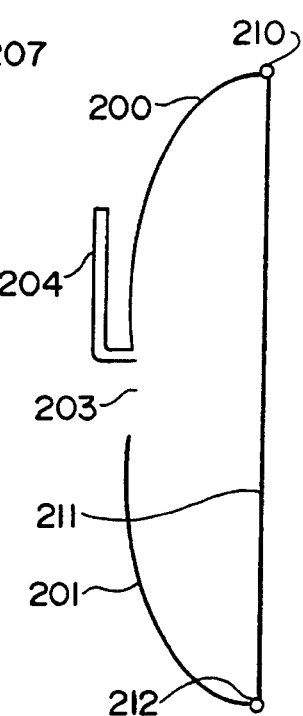
FIG. 6
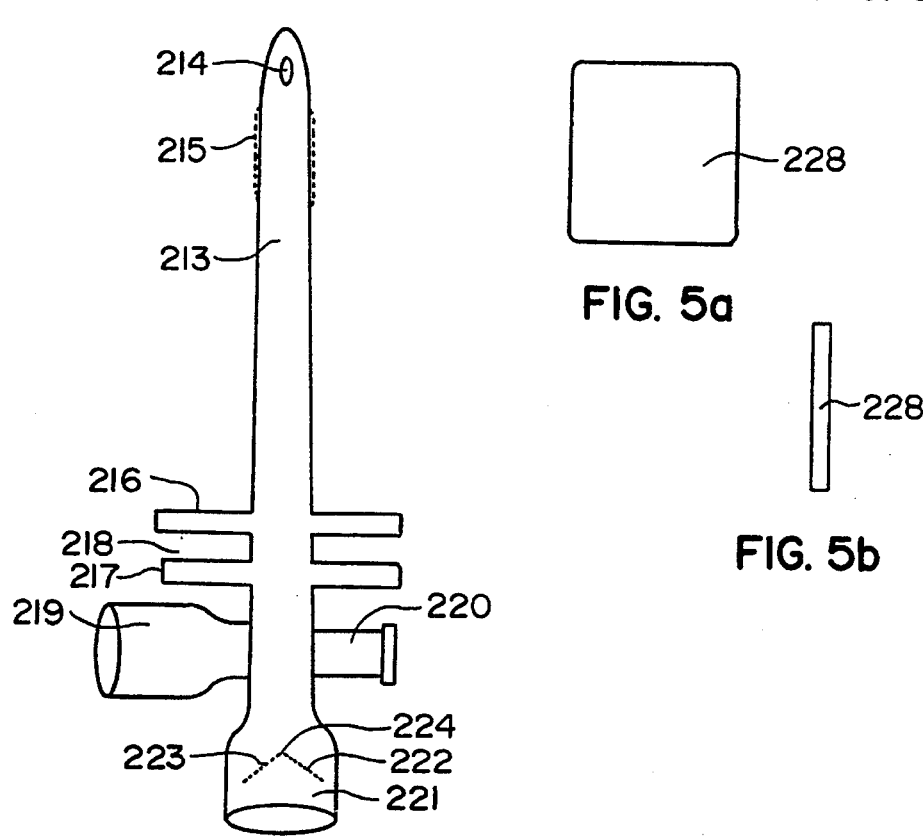
FIG. 5a
FIG. 5b
FIG. 7

URINARY CATHETERS, AND SUPPORT SYSTEMS THEREFOR

BACKGROUND

Problems of the bladder and urethra are very common and the use of Foley catheters is a daily routine in hospitals. However, standard Foley catheters have their own problems and complications. They are loose and unprotected, which is wrong and problematic, many times being held in place by use of adhesive tapes to tape them on the thigh area. However, using adhesive tapes has its own problem with irritation of the skin, allergies, and pain of removing them and pulling hairs under them.

But there is also another and much more serious problem which occurs when a confused, irritated patient pulls his or her catheter out of the bladder. This causes significant injuries in the area and significant complications, which are painful and costly to be dealt with. This action of pulling a catheter with a dilated balloon in its tip through the urethra of a patient is a serious problem that is mostly ignored, although it commonly causes significant damage to the patient's urethra. In some cases such as confused older patients, the damages of such action may not be truly recognized due to the patient not being able to express the problem, lack of detailed exam, and tendency to ignore the problem. In males, it may cause much pronounced damage. Therefore such problems should be avoided at all cost because prevention is usually easier and cheaper. Another problem with standard Foley catheters is that they are either in or out, and when in, the patient has to tolerate the placement.

BRIEF SUMMARY OF THE INVENTION

The invention relates to a new bladder catheter that has separate parts that can be disconnected easily to give freedom of using a small catheter alone, without tubing and urine collection bag. The catheter also has a support system to hold it in place with use of straps and wraps that will prevent and resist the catheter being pulled out of the bladder. The lower end of the small catheter has a valve or three-way stopcock that can be closed to prevent free flow of urine. The three-way stopcock will allow selective irrigation of the catheter and outside tubing, and also allow culture sample to be done selectively. The support system, tubing and collection bag can be removed temporarily to allow a patient to take a shower or move around more freely. An alarm system will help the medical personnel to know if a patient has pulled the tubing.

Also introduced are a support system and adaptors that allow presently used standard Foley catheters to be used and held in place much more securely and steadily and to resist the catheter being pulled out.

Also introduced is a new collection bag that can be carried easily inside a regular looking hand bag to make the use of such units more socially acceptable.

BRIEF DESCRIPTION OF THE DRAWINGS

FIG. 5 shows a front view of a part used in a modified form of catheter.

FIGS. 5a and 5b show front and side views respectively of a part used with the part of FIG. 5.

FIG. 6 is a cross section taken along lines 6—6 in FIG. 5.

FIG. 7 shows a fifth embodiment used with the part of FIG. 5.

EXPLANATION OF THE FIGURES

Figure 1:
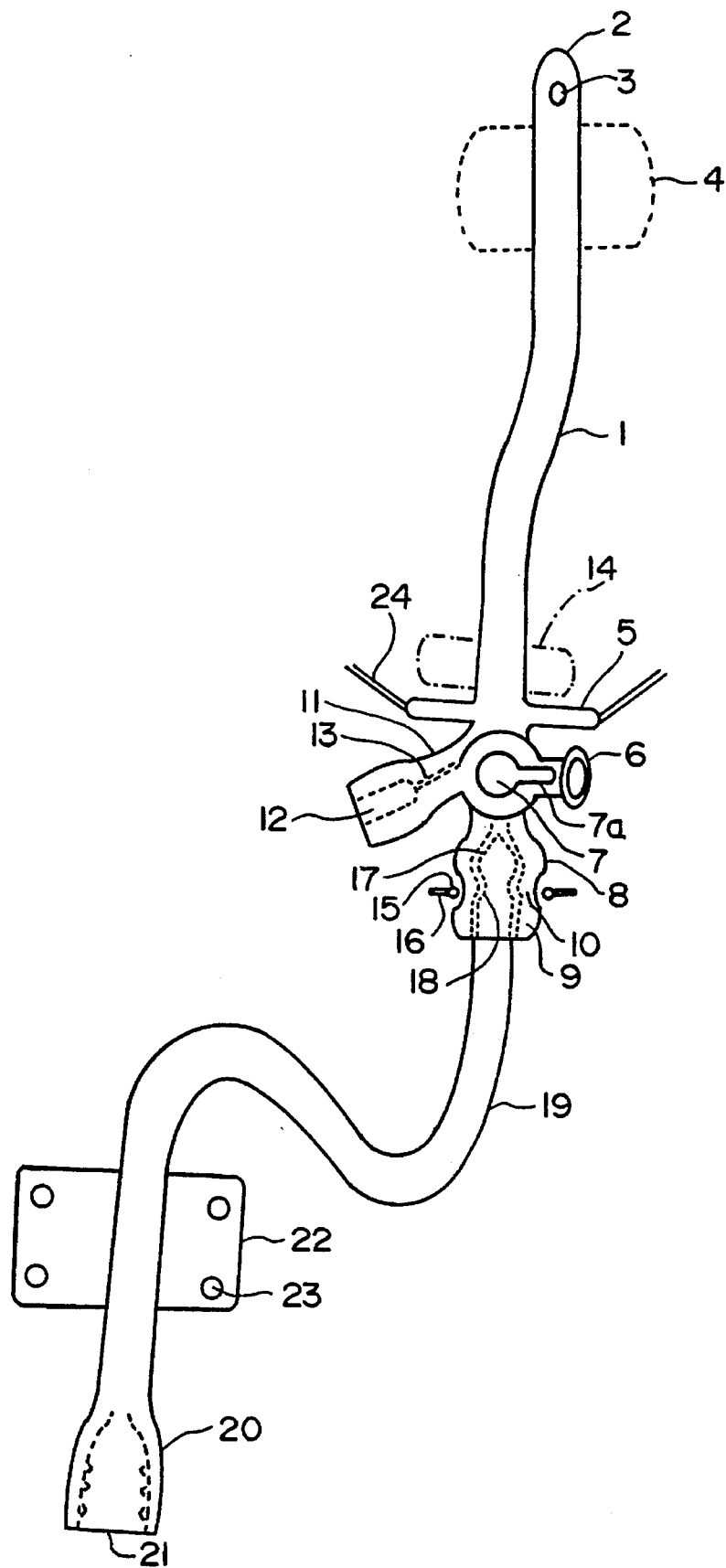
FIG. 1 shows a first embodiment of catheter without full details of the support system.

FIG. 1 shows a new Foley catheter 1 (which the inventor calls "Safe Catheter") having a tip 2 and a balloon 4. The body of catheter 1 extends to a shield 5 that limits insertion into the urethra. A soft balloon 14 can be inserted to protect the tip of the penis and fill the space between it and the shield 5. Shield 5 is made from the same material as catheter 1, or harder plastic that allows connection of straps 24 to its ends by having holes in the corners. This is to allow it to be hooked to straps when desired.

Just beyond shield 5, a three-way stopcock 7 has an opening 6 in the right side that is shaped to accept the tip of a standard syringe. The handle of the three-way stopcock is shown at 7a and can turn in different directions. In the other side of the three-way stopcock, there is an inflation port 12 that is communicated by a narrow inflation passage tube 13 to balloon 4. Tube 13 runs inside the catheter, and the inflation port has a valve (not shown) that will open when tip of a regular syringe is pressed against it, and that will close when the syringe is removed. This syringe delivers about 5–10 ml of water inside balloon 4.

Catheter 1 ends at a female end piece 8 that is expansible for accepting the male end 17 of a lower tube 19. A circular raised area 10 around the inside of end piece 8 will match an indentation 18 at the tip of lower tube 19. A circular indentation around the exterior of end piece 8 at the location of area 10 allows a rubber band 15, or a metal spring, to be placed to tighten the grip of the lower end of catheter 1 on the tip of tube 19, and also to close the opening of female end piece 8 after tube 19 has been removed.

Tube 19 extends for a certain length from tip end 17, continuing to have a flat latex piece 22 on the outside of its wall. Piece 22 has holes 23 to allow it to be hung or positioned inside a plastic cradle to hold it stable in the thigh area. The lower end of tube 19 is shown at 20 and has an opening 21 with indentations inside it to grip the end of a further tube (not shown) leading to a urine collection bag.

Figure 2:
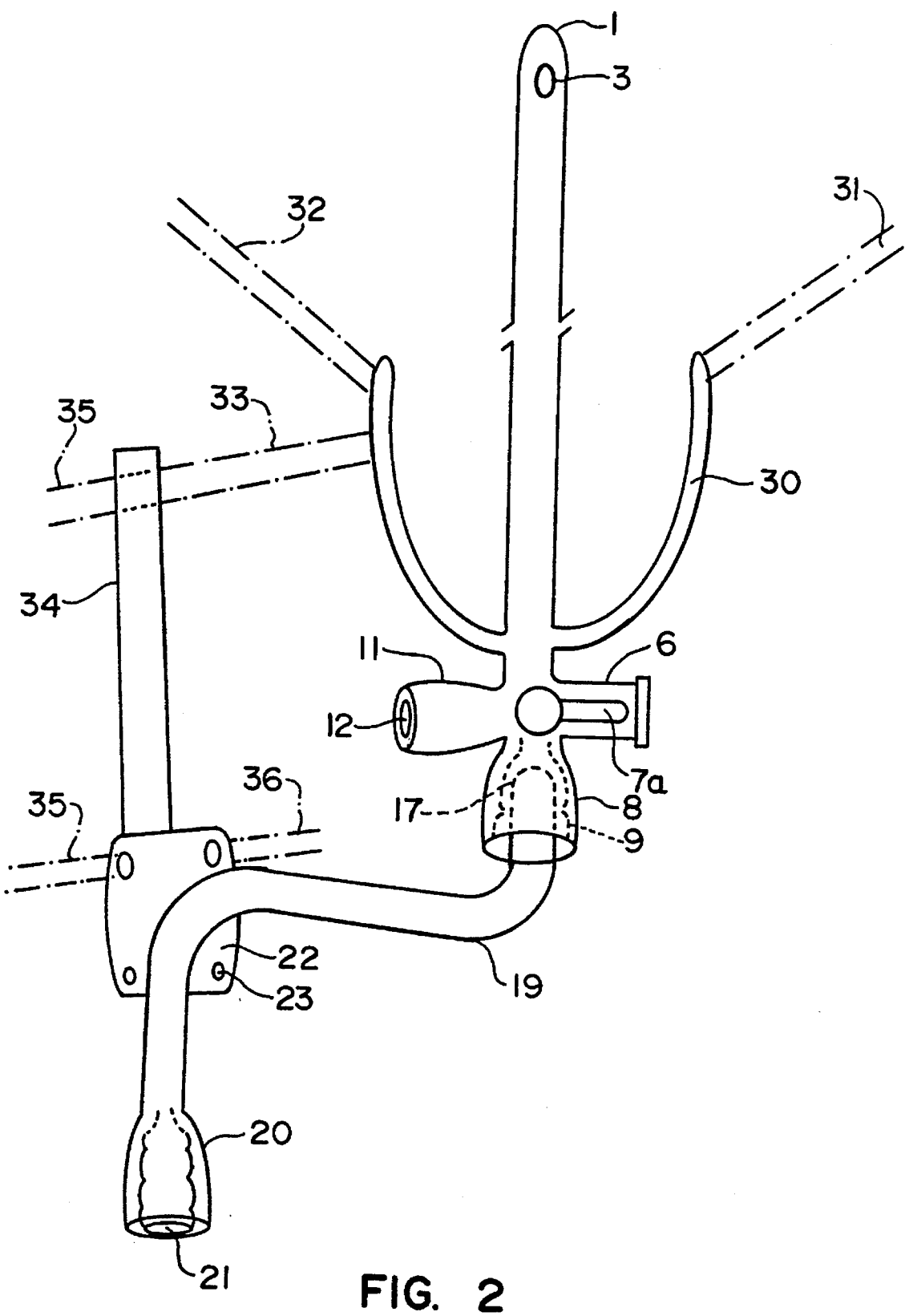
FIG. 2 shows a second embodiment with some detail of the support system.

FIG. 2 is very similar to FIG. 1 except that shield 5 is replaced by a half egg shell-shaped shield 30 to allow use of some medications, such as local anesthetics, such as xylocaine jelly and/or certain antibiotics in some cases, to be placed in the tip of this shell to let the tip of the opening of the urethra be exposed to them for their soothing and therapeutic effects.

Shield 30 is made from soft latex and has holes or places in its rim area to allow straps 31, 32, 33 to be connected so that the unit can be held on the tip of the penis with more stability. These straps are an upper pair 31, 32 that go around the waist, and a lower pair 33 that go around the upper thigh area. Beyond shield 30 are the three-way stopcock 6 and its handle 7a, and on the other side, the opening of the inflation port 12 (which are combined here for easier handling), and end piece 8 is the same as in FIG. 1. Lower tube 19 is the same except it has a place in its piece 22 that is connected by a strap 34 to the upper straps 33–35. There can also be another shell (not shown here) to go over the three-way stopcock and lower end to protect them from the trauma and related discomfort to patient.

Figure 4A:
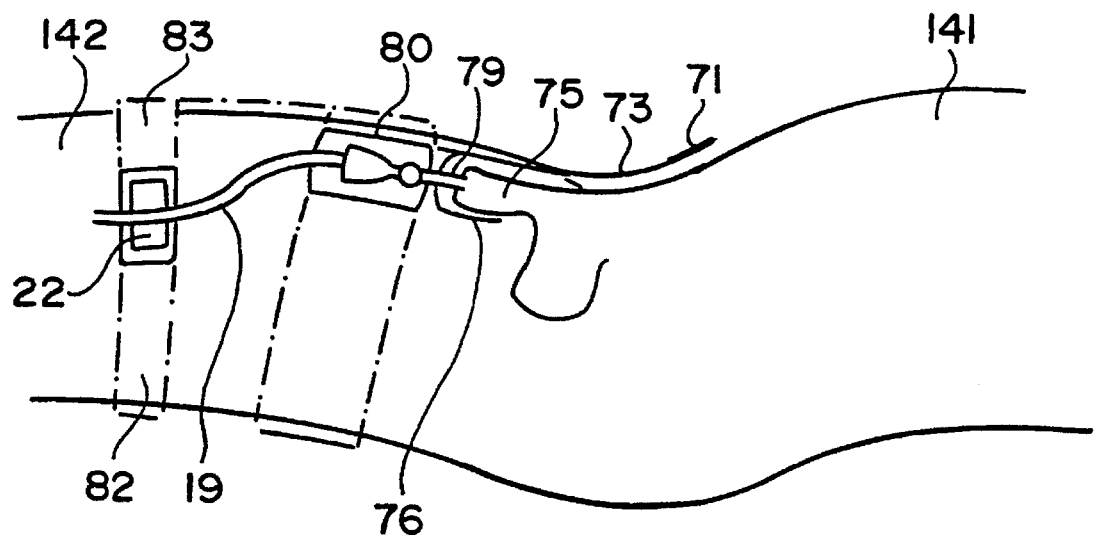
FIG. 4a shows a side view of the fourth embodiment in use.
Figure 4:
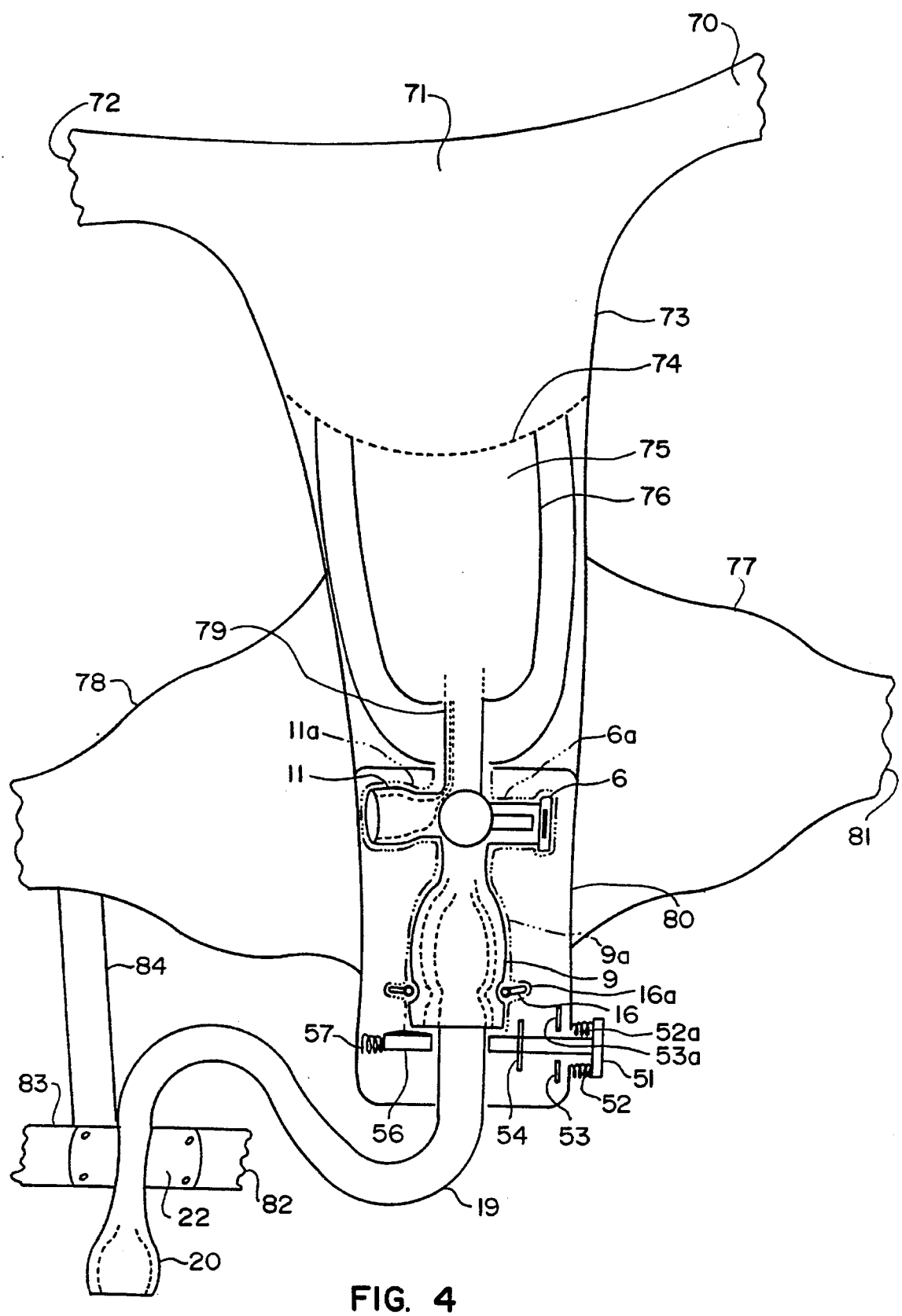
FIG. 4 shows a fourth embodiment with some detail of the support system.

FIG. 4 shows a catheter used with a support system that is larger and designed to be more sturdy and stable. It starts from a base 71 that is made from a woven non-stretchable synthetic material with a soft surface that will stay in the pubic area and has straps 70, 72 that go around the waist to hold it in place. In the lower end of such support system there will be a shell 76 somewhat similar to the one in FIG. 2. It can be non-stretchable, but may have a soft surface made from small mosaics of balloons or a cover with soft material such as cotton, to prevent trauma or irritation of the penis. The catheter 79 comes out of penis 75 to enter a compartment 80 made from a hard plastic. It has spaces like cradles that allow the components of the lower end of the catheter to be positioned and held inside it. Close to the lower end of the catheter is a piece 56 with a cover that will close the lower end opening of the catheter so that if the tip of lower tube 19 is removed, this piece 56 will be pushed to make a metal piece 54 to contact pieces 53 and 53a and complete an electric circuit that causes an alarm to be activated to notify medical staff. Springs 57, 52, 52a push piece 54. At the time of insertion of the catheter, a button 51 is pressed to align an opening of piece 56 with the place of tip of the lower tube. The electric circuit is therefore disrupted when the tip of lower tube 19 is in place. The plastic compartment 80 and its supportive straps 77, 78 can be removed temporarily to allow the patient to take a shower. Also if the patient is no longer confused, lower tube 19 can be connected to the tube of the collection bag to be used very much like a regular unit. Lower tube 19 is held on the thigh when latex piece 22 is strapped around the thigh by straps 83 and 82. A piece 84, which may be hard, will prevent it from moving up and down.

This unit will be tailored skillfully to stand on one thigh or another to be secure and comfortable. And then naturally the tip of the penis will be tilted to that side. And the rest of the unit will also have the necessary alignment and curbings in their construction to allow a comfortable functional unit to be made. The wrap 77, 78 will be designed to stand on one thigh and its extensions to go around it.

FIG. 4a shows wrap 71 over the pubic area to hold the unit more securely. It then continues with the extension 73 followed by cover 76 that is around the penis 75. Catheter 79 leaves the urethra and enters into the plastic compartment 80. Inside this compartment the lower end of catheter 79 is connected to the tip of lower tube 19, then the lower tube of 19 leaves the plastic compartment and goes to have the piece 22 held by straps 83, 82 around the thigh. The plastic compartment is also held in place by straps 77 and 78.

Figure 3:
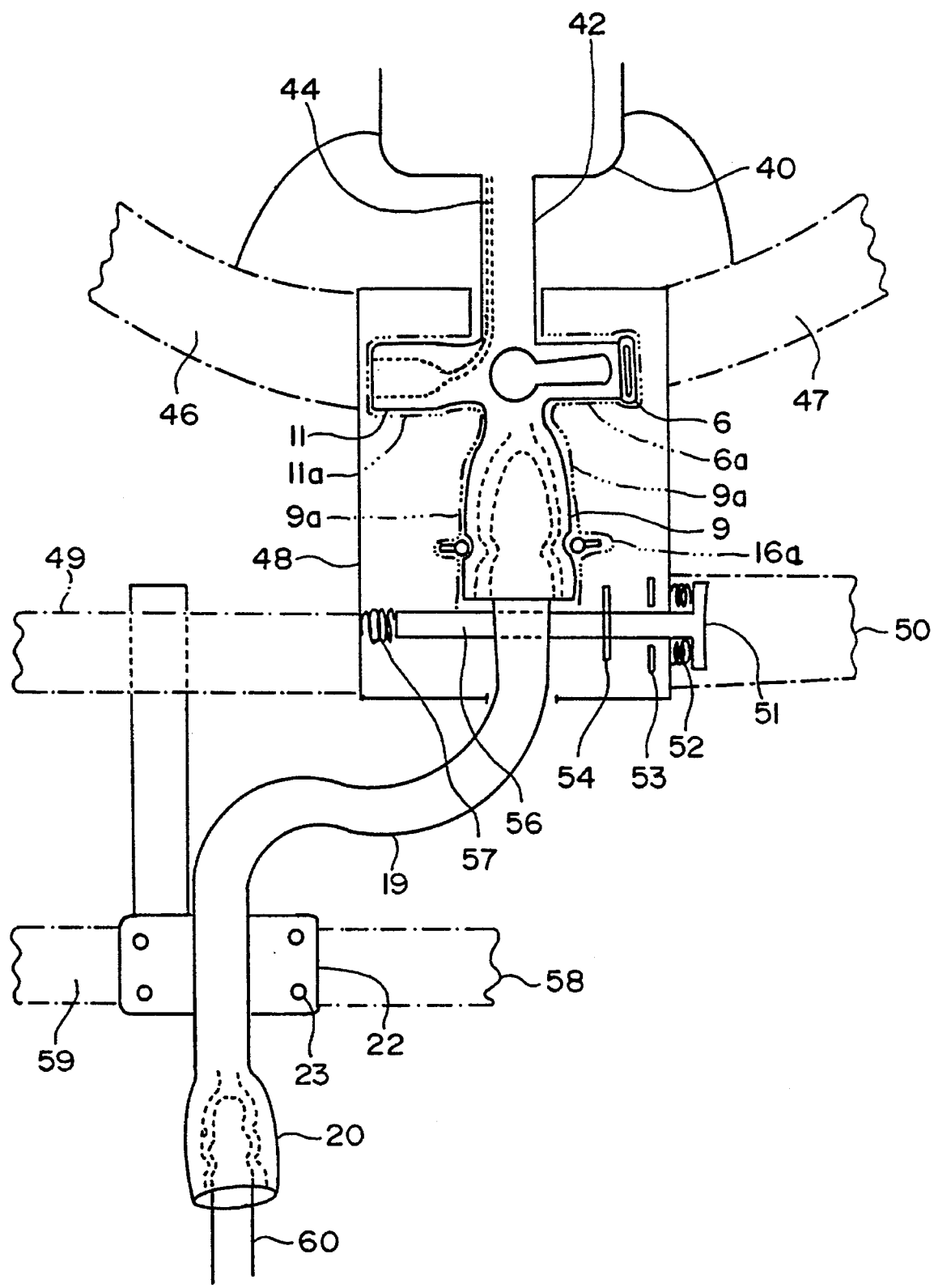
FIG. 3 shows a third embodiment with some detail of the support system.

FIG. 3 shows a catheter unit that has a construction very similar to the unit shown in FIG. 4 except this is a unit to be used in female patients. Therefore the length of the catheter is naturally shorter and the support system is also shorter in its length (due to the lack of penis). Otherwise it will be very much similar to the unit shown in previous FIG. 4. Here again the support system is made from woven non-stretchable synthetic material with a soft cover that will stay in the pubic area to be held by straps 46, 47 that go around the waist to hold it in place. The catheter 42 comes out of urethra, then it enters the plastic compartment 48. The plastic 48 compartment has cradles with walls such as 6a, 9a, 11a, 16a that will let the lower parts of the catheter 6, 9, 11, to be situated inside it, also when the tip of the lower tube is inserted into it. A plastic piece 56 is designed that may move and close the opening of the end of the catheter if the tip of lower tube 19 were removed. This same piece 56 is pushed to make an electric circuit to be completed and an alarm to be activated. This alarm will have an electric circuit that is disrupted when the tip of lower tube 19 is in place. When the tip of the lower tube is pulled, then spring 57 will push piece 56 to move forward and to close the opening of the catheter, and also to connect two ends 53 of an electric circuit together by its metal piece of 54 to make the alarm function. The springs 52 will also push the piece 51 to help this system to function. When the lower tube is to be placed into the place inside the plastic compartment, this tip 51 has to be pushed in to allow the tip of the lower tube to go through.

Figure 3A:
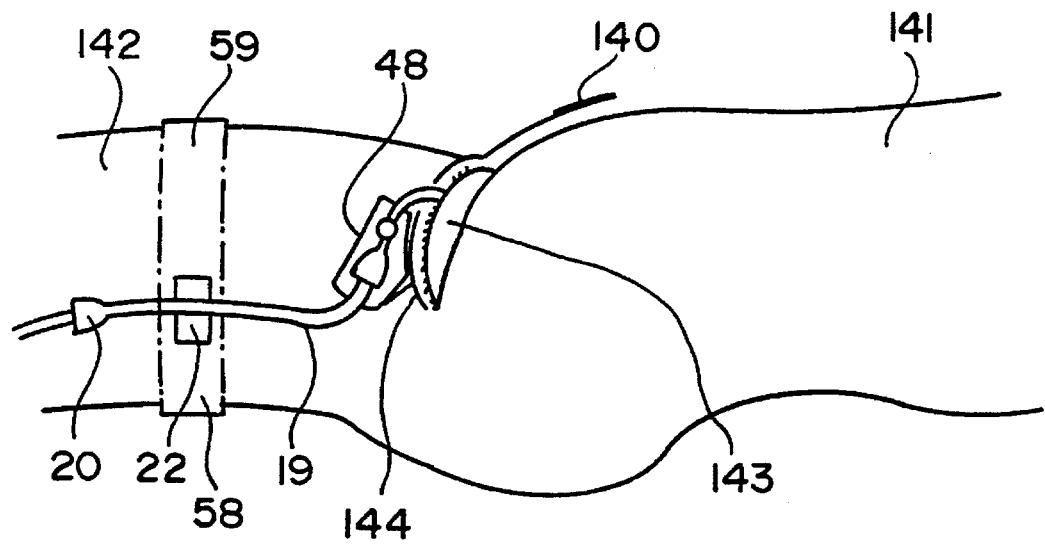
FIG. 3a shows a side view of the third embodiment in use.

FIG. 3a is similar to FIG. 3, except it has a wrap 140 in the pubic area to hold the unit more securely. The body is shown by 141 and the inner surface of right thigh by 142. The external female genitalia is shown by 143. Here the surface of the external genitalia is covered by a support cover 144 which is an extension of wrap 140. The support covers almost all external genitalia of the female patient to make a secure base for holding the catheter and plastic compartment. The cover has a hole that allows the catheter which leaves the urethra to go through cover 144 and enter compartment 48 which will be tightly attached and secured over cover 144. This attachment will be secure so that the patient cannot remove it. The cover of the compartment will also be secure so that the patient cannot open it. Then the lower tube 19 leaves the plastic compartment and continues to have the piece 22 held by straps 59 and 58. The end of tube 19 is shown by 20.

FIG. 5 shows a support unit that is designed to be used with the catheter shown in FIG. 7 which has pieces 216 and 217 in the shape of an H. They allow the catheter to be held in place securely. The unit shown here is for use by females whose urethras do not vary much. (This will allow a couple of sizes to be made for use. A modified unit can be used for males with an adaptor that adjusts the length of the catheter.) This support cover of FIG. 5 will match and stay over the whole area of the external female genitalia. Here the upper part is shown by 200, and the open area from top to the center by 202. This allows the cover to go over the catheter that is already inserted inside the bladder with the catheter fitting in the center hole 203. A slot is defined by a front U-shaped piece 204 connected by a lower wall 205 to the cover. After the catheter is in place, a small piece of plastic 228 shown in FIGS. 5a, 5b is slid into the slot defined by 204–205 to prevent the catheter from moving up. One strap may go over this plastic to hold it completely secure. A small door may also be used instead of the sliding plastic to do the same job. The straps for holding the support system are 206 and 207 that goes over on the waist area, and 208 and 209 that go around the thigh.

FIG. 6 shows the cover 200 with its upper edge 210 and lower side 201 and lower edge 212. The rim is shown by 211. The curved face in the left side has the matching shape of the external female genitalia.

Figure 15:
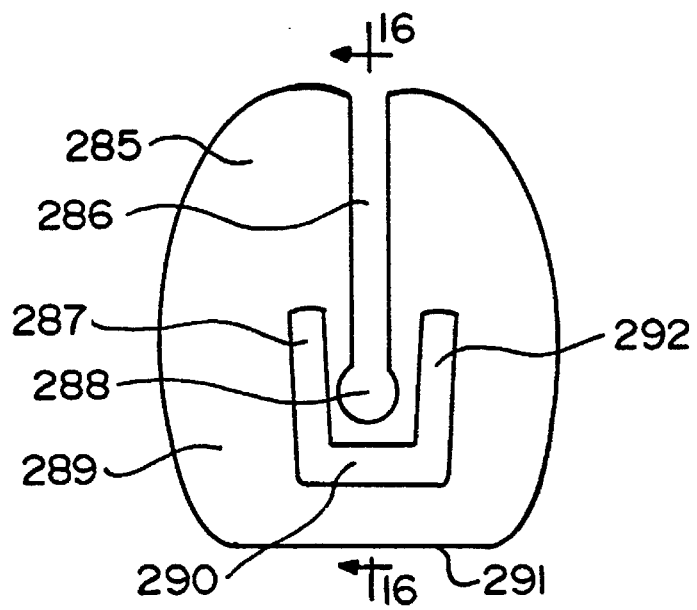
FIG. 15 shows a support cover for use with a female patient.
Figure 16:
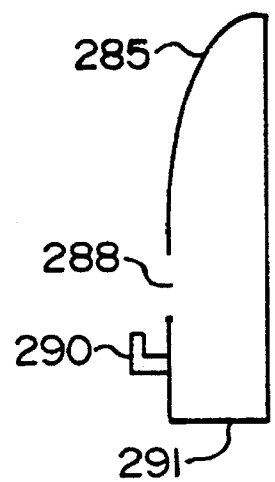
FIG. 16 is a cross sectional view taken along lines 16—16 in FIG. 15.

FIG. 7 shows the catheter designed to be used with the support unit shown in FIGS. 5 and 6, as well as a support unit shown in FIGS. 15 and 16. This catheter is very similar to the catheter shown in FIG. 1. The material, general shape and construction are very similar, except that this unit has two flat pieces 216, 217 that substitute for piece 5 in FIG. 1. These pieces will be flat circular or rectangular pieces of latex of about 3 to 4 mm thick and a diameter or side of about 2.5 to 4 cm, with a shorter distance 218 of about 4 to 6 mm or so from each other. This distance 218 is to match the thickness of the support system so that the support system can be comfortably positioned between these two pieces, and prevent catheter movement. Then the three-way stopcock 220 and the inflation port of the balloon 219 and opening of the catheter 221 will be located. This view also tries to illustrate a one-way valve 222, 223, 224 that is inside opening 221 to make the catheter close when the tip of the lower tube 19 is out.

Figure 8:
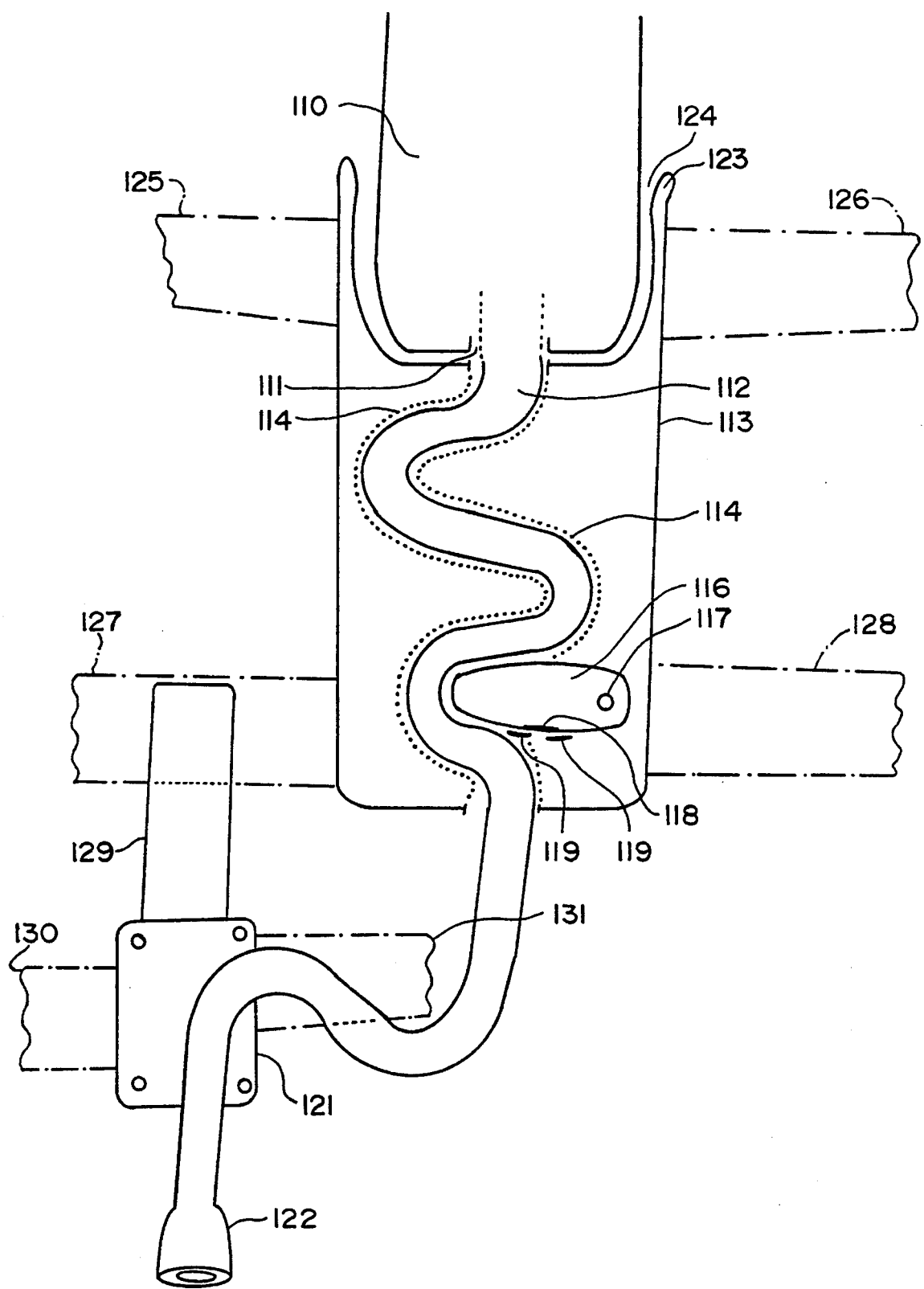
FIG. 8 shows a sixth embodiment.

FIG. 8 shows a support unit for use with presently used standard Foley catheters. This unit holds a catheter securely in place and significantly diminishes the chance of pulling it out. This unit is made from combinations of soft materials, such as latex, which may have a core of woven non-stretchable materials, and a plastic compartment made from harder plastic that may be covered by fabric or non-stretchable material. It is to be held in place securely by straps 125, 126 that will go around the waist, 127, 128 around upper thigh, and 130, 131 around mid to lower thigh. This unit has a shield 123 to cover the tip of the penis 110 to prevent a male patient from being able to reach the tip of the Foley catheter 112 which is inside the meatus 111. The Foley catheter then will enter inside a plastic compartment that has a cradle made from hard plastic that will hold it in place tight without letting it to be pulled due to the design of the cradle. Pulling the catheter will force it against the wall of the cradle which is not slippery and will resist and prevent movement of the catheter. After a couple of turns 114 inside the cradle, the catheter may be exposed to a trap 116 that is held by a spring (not shown here). This trap will be pulled down toward the lower end of the plastic compartment if the lower end of the Foley catheter is pulled. This trap 116 is hinged to the back wall of the plastic compartment by pole 117 which functions as a hinge that will allow the piece 116 to rotate around it. Trap 116 has a conductive metal piece 118 that will touch the two conductive metal pieces 119 when the piece 116 is pulled down by the pulling of the Foley catheter. The contact of these metals will make a circuit complete to make an alarm to sound, and to give a signal to medical personnel that the patient is pulling the Foley catheter. After leaving the plastic compartment, the catheter is held in place around the thigh by another molded piece 121 that will hold the Foley catheter securely inside itself, to prevent it from being pulled. Both the plastic compartment and the piece 121 will be covered by a matching door to hold the catheter securely tight inside itself. Piece 121 may be made to have more curve in its surface than shown. The piece 121 will be held on the thigh securely by straps 130 and 131 and is connected to upper strap 127 by piece 129 to prevent it from moving down. Piece 129 may have hard components that will not allow its length to be diminished and the piece 121 to move unwantedly. A wrap may be used to hold the whole unit on itself securely and more steadily. The ends of the wrap may be held in place with use of straps.

I would like to mention that in this unit as well as the other units mentioned in this application, the ends of straps may be held together with use of conventional methods, such as snaps and/or Velcro™ system. However in cases where a patient may be confused, the ends of the straps will be secured further with putting them inside a plastic cover that will be hard to be opened by a patient and it will be even tightened further by taping the plastic cover by an adhesive tape that will go over them. The wraps will be made from materials with a soft non-irritating surface that will not bother the skin of the thigh.

Figure 8A:
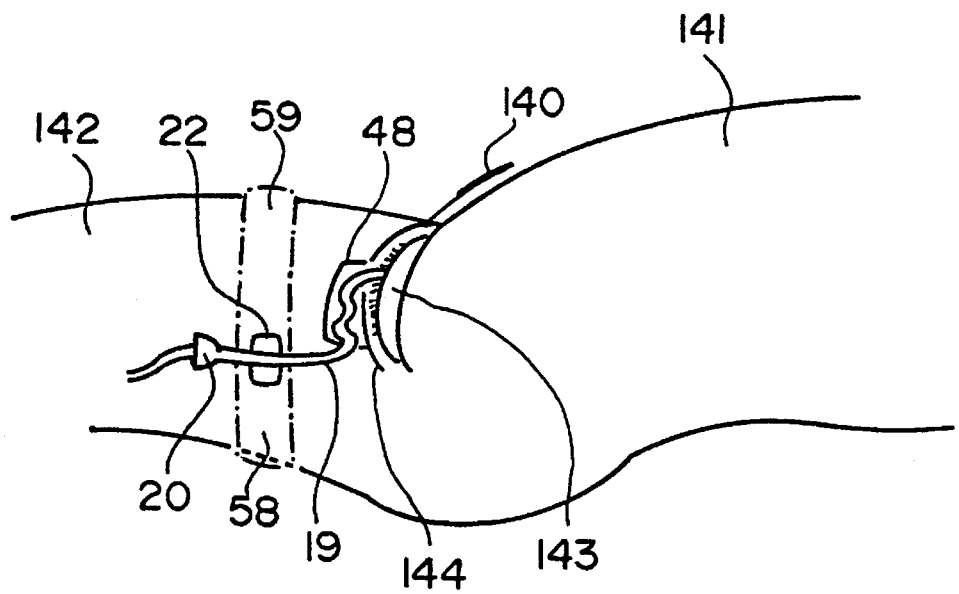
FIG. 8a shows a side view of a catheterized female patient wearing a female version of a support system similar to the one shown in FIG. 8.

FIG. 8a shows a modified version of the support system of FIG. 8. In this view the body of a female is shown by 141 and the inner surface of right thigh by 142. The external genitalia is shown by 143. Here the surface of the external genitalia is covered by the modified support cover 144 which is the extension of the wrap 140. This covers almost all external genitalia of the female patient to make a secure base for holding the Foley catheter and plastic compartment. The cover 144 has a hole that allows the catheter which leaves the urethra to go through the cover and to enter into the plastic compartment 48 which will be tightly attached and secured over the cover 144. This attachment will be secure so that patient could not remove it. The cover of the plastic compartment will also be secure so that patient cannot open it. Then the lower tube 19 leaves the plastic compartment and continues to have the piece 22 and be held by straps 59 and 58. Its end is shown by 20.

Figure 8B:
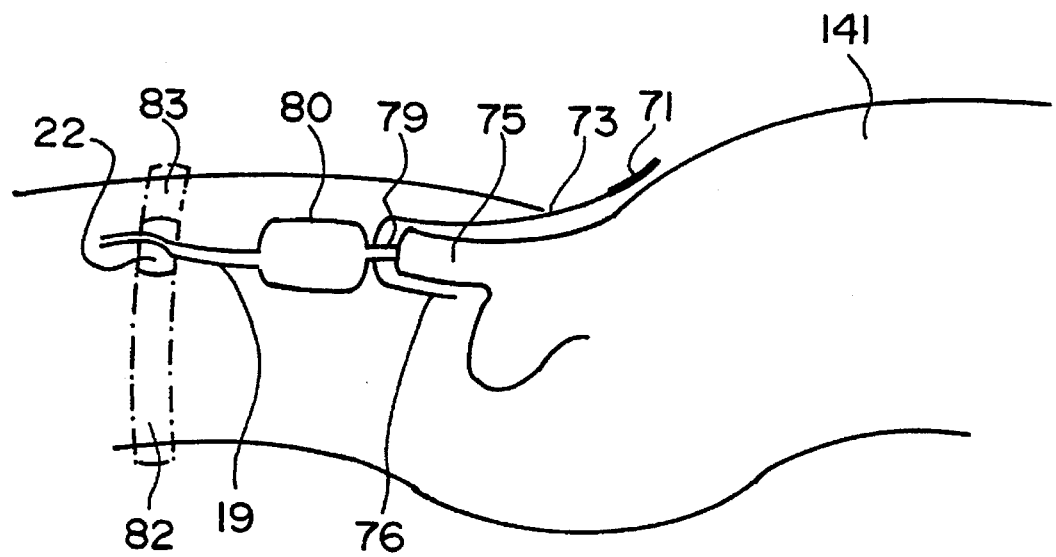
FIG. 8b shows a side view of a catheterized male patient wearing a male version of the support system.

FIG. 8b shows a male patient who is wearing a unit similar to the one shown in FIG. 8a, that is modified for a male patient. In this view the wrap 71 is over pubic area to hold the unit more securely. It then continues with the extension 73 followed by cover 76 that is around the penis 75. The Foley catheter 79 leaves the urethra and enters into the plastic compartment 80 which holds the catheter inside its channel, then the Foley catheter 19 leaves the plastic compartment and goes to piece 22 that is held by straps 83 and 82 around the thigh.

Figure 9:
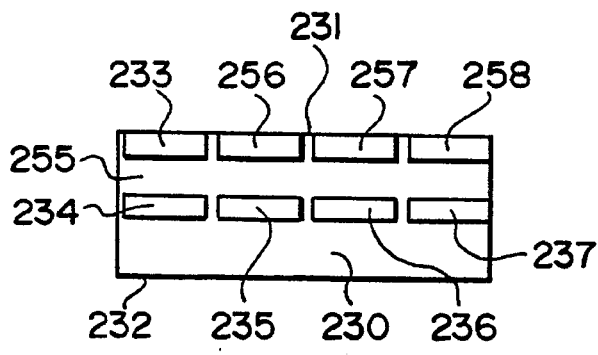
FIGS. 9, 10 and 11 show various views of an adaptor that goes on a standard Foley catheter to adapt it for the support system of FIG. 8.
Figure 10:
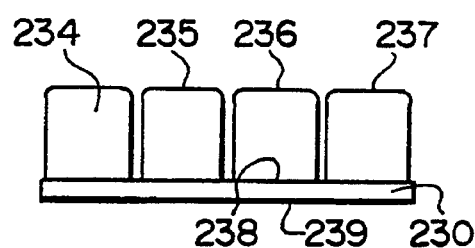

FIGS. 9 and 10 show an adaptor made from latex, rubber, or similar material; it may also have a component of hard plastic inside. This piece is made to be wrapped around the outside of a standard Foley catheter so that the catheter can be held in place tight by the support unit of FIGS. 5 and 6. The body of the adaptor is shown by 230, the rear edge by 231, the front edge by 232, the rear walls by 233, 256, 257, and 258, the front walls by 234, 235, 236, and 237, and the space between them by 255. The upper edge of the body is 238, and the lower edge is 239.

Figure 11:
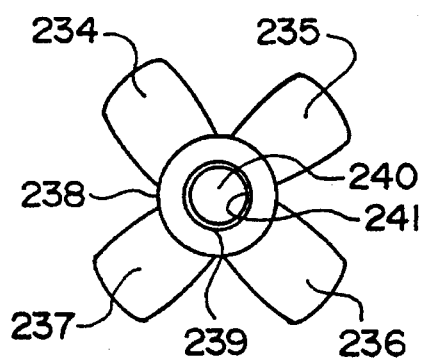

FIG. 11 shows the adaptor when it is in place on a Foley catheter. The inner lumen of the catheter is shown by 240 and the outer surface by 241. The lower surface 239 of the adaptor is shown sticking on the outer surface of the catheter. The shape, length and size of the 234, 235, 236, and 237 short walls may be varied for specific usage.

Figure 12:
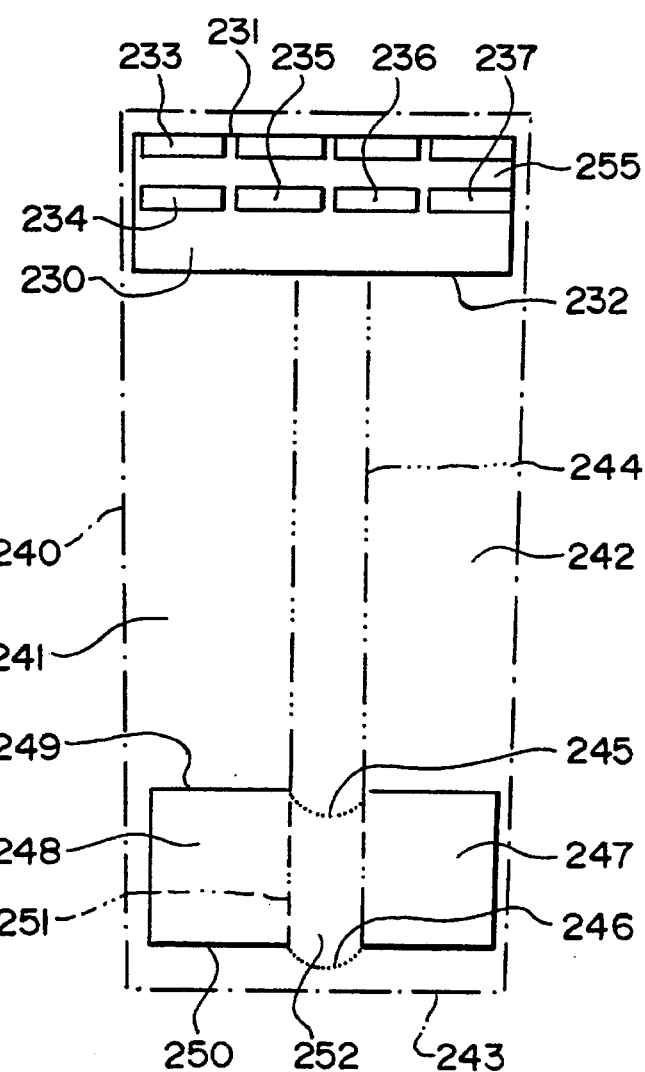
FIG. 12 shows a fixture for holding the adaptor of FIG. 9 during attachment to the Foley catheter.

FIG. 12 shows a fixture which is designed to simplify attaching the adaptor on the catheter. This fixture is made from a layer of soft or hard plastic that has a place for insertion of the adaptor at one end and also a piece 247 that goes over the lower part of the catheter at the other end. Between these two, there is a cradle 244 for placement of the Foley catheter. At the time of use the rear face of this fixture will be opened to expose the surface of piece 247, and a cover on the lower surface 239 of the adaptor will be removed to expose an adhesive surface. Then the Foley catheter is positioned in cradle 244 and the adaptor is rolled to go around the catheter, with body 230 being stuck to it.

Figure 13:
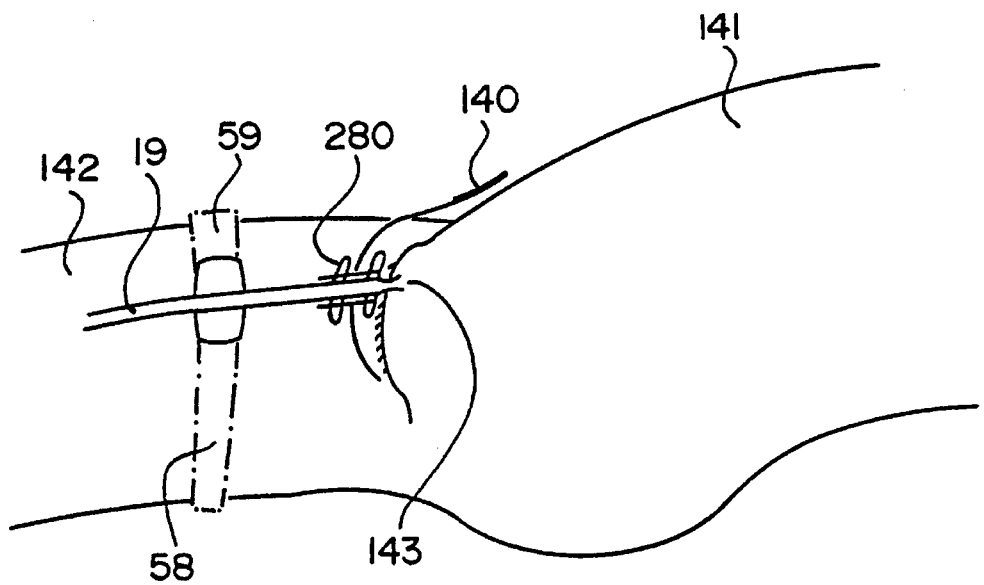
FIG. 13 shows a side view of a female patient with a Foley catheter that has the adaptor of FIG. 9.

FIG. 13 shows a female wearing the unit shown in FIGS. 5 and 6, but with a standard Foley catheter having the adaptor on it. The body is shown by 141, the inner surface of the right thigh by 142, and the external genitalia by 143. The external genitalia 143 is covered by the support cover 144 which is an extension of the wrap 140. This unit covers almost all external genitalia of the female patient to make a secure base for holding the catheter and plastic compartment. The catheter comes out of the urethra and is covered by the Foley adaptor 280 which is held tight by the support system, and it continues to be held in place on the thigh by straps 58, 59.

Figure 14:
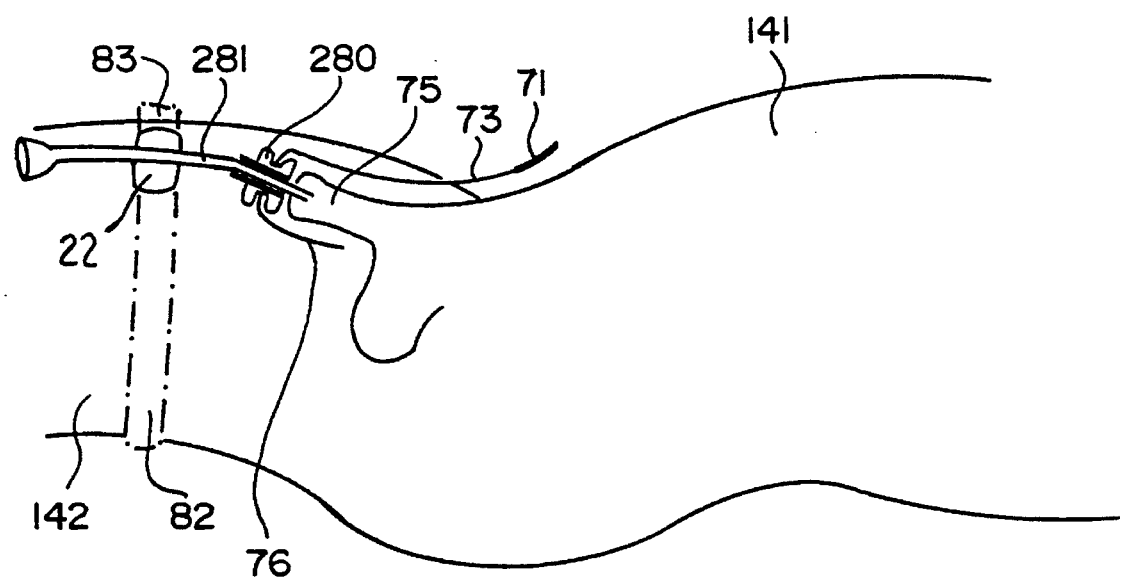
FIG. 14 shows a side view of a male patient with a Foley catheter that has the adaptor of FIG. 9.

FIG. 14 shows a male patient who is wearing a support unit very similar to the one in FIG. 4a, except here the patient has a standard catheter 281 modified by the Foley adaptor 280 that allows it to be used by this support unit. The body is shown by 141, and the inner surface of the right thigh by 142. The wrap 71 is over the pubic area to hold the unit more securely. It then continues with extension 73 followed by cover 76 that goes over the penis 75. The catheter 281 leaves the urethra and is covered by adaptor 280 which stays in place tight inside the matching opening of the cover 76 (which is modified to allow this to happen, with having a compartment shape). Then the catheter continues to be held in place securely when it goes into the piece 22 that is held in place by straps 83 and 82 around the thigh.

FIGS. 15 and 16 show a support unit that is designed for use with a standard Foley catheter to hold it securely in place after the adaptor of FIG. 9 is placed on its surface. The construction of this unit is similar to those previously mentioned and shown in FIGS. 5 and 6. This is a unit designed primarily for a female, but also shows how a physician can have the option to adjust the length of the catheter so that the catheter will not be pushed too far inside the bladder. For this reason the adaptor is used to gently pull the catheter outside and hold it in proper place. In order for the adaptor to stay on the support cover, a slot for sliding a spacer (FIG. 17) is provided. At the time of use the catheter is placed inside the bladder and a right size spacer is placed on the cover and the cover is moved so that the catheter and adaptor will slide and stay inside the cover. A matching cover will go over the adaptor and spacer to form a compartment to hold the catheter in place. In these FIGS. 15 and 16 the cover covers only the upper ⅘th of the external genitalia. Its upper part is shown by 285, the open mid part by 286 and the center hole by 288. The right side of the slot by 287, the lower part of slot 290, the lower right side of the cover by 289, the lower rim of the cover by 291, and the left side of the slot by 292.

Figure 17:
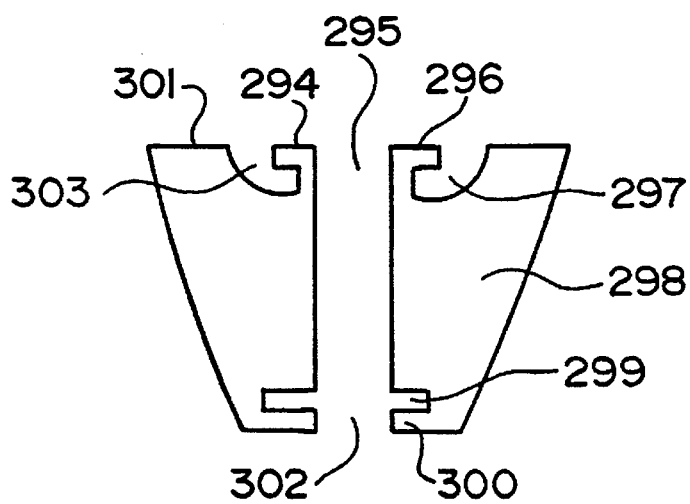
FIG. 17 shows a cross section of a part used in association with the part of FIG. 15.

FIG. 17 shows a top view of the spacer mentioned earlier in connection with FIGS. 15 and 16. This shows two short walls 294 and 296 that will slide inside slots 287 and 292. The open center 295 is for the catheter and the opening near the tip 299 is for the piece 233–257 of the adaptor shown in FIGS. 9 and 10 to be inserted, and to be held in place securely. The piece 300 will match and fit the opening 255 of the adaptor shown in FIG. 9. Tip 302 is for the catheter to leave this unit. The side 298 is also shown. This spacer will be made with different lengths to allow a proper length to be chosen and used.

Figure 18:
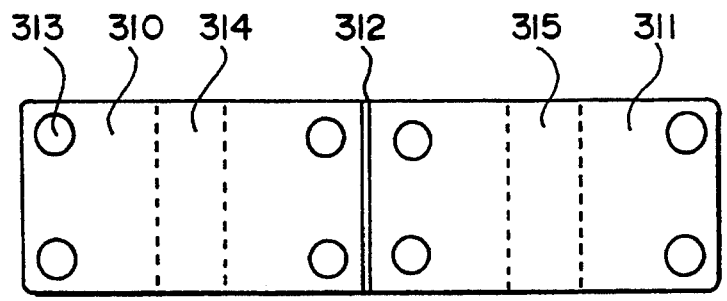
FIGS. 18 and 19 show plan and front views of an adaptor for holding a Foley catheter on the thigh area.
Figure 19:
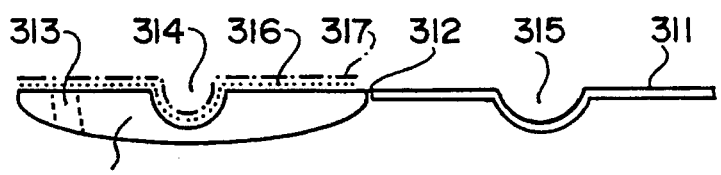

FIGS. 18 and 19 show another adaptor for a standard Foley catheter that will hold the body of the catheter inside it and be held on the thigh area by straps or a support unit. The body of this adaptor is shown at 310. Its cover 311 is connected by a narrow connection 312 that will allow cover 311 to be folded over and stuck to body 310. 313 shows one of the holes in the corner. 314 and 315 are cradles for the Foley catheter's body to be situated in. Body 310 has a surface covered by a film of adhesive material 316 that is covered by a thin layer plastic that is removably stuck to the surface of the film of adhesive to protect it. At the time of use the cover of the adhesive is removed, the catheter is placed in cradle 314, and cover 311 is folded along line 312 to stick onto body 310.

Figure 20:
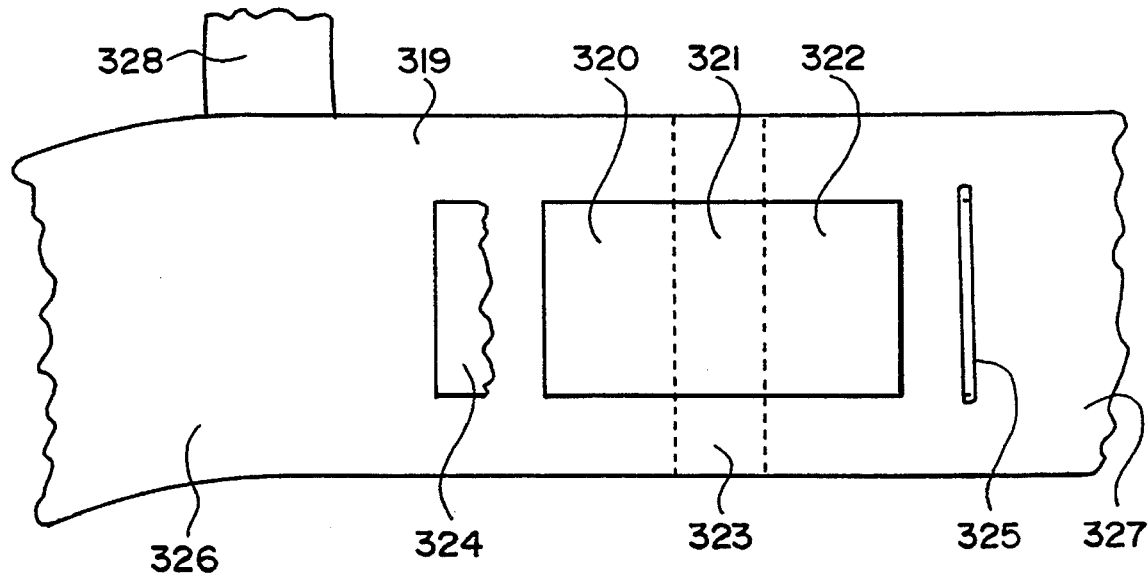
FIG. 20 shows a plan view of a portion of strap which has the adaptor of FIG. 18.

FIG. 20 shows a strap for holding a Foley catheter which has the adaptor of FIGS. 18 and 19 on it. The strap 326, 327 has a cradle 323 for the adaptor to sit inside it. The strap 326, 327 goes around the thigh area and to come and are connected to each other by a snap or Velcro™ system, that can be protected by a plastic to prevent it from being opened. Strap 328 is to be connected to the straps that are around the waist area to prevent the unit from being pulled down on the thigh, and this piece may have hard plastic as part of its wall. 324 is a narrower strap that will go over the adaptor when the adaptor and Foley catheter are in place. Then the end of this strap 324 will go through a narrow bridge of 325 to make a U-turn to come and stick to its own back. This point may be strengthened by use of a strong adhesive, or a Velcro™ taping may be used instead to be covered by an adhesive tape on it.

DETAILED DESCRIPTION OF THE INVENTION

This invention introduces new and safer bladder catheters as well as a support system and related units that basically will help to prevent the serious and costly problems of pulling and removal of bladder catheters by confused, irritated patients. One feature of the new catheters allows the tubing and urine bag to be disconnected easily and temporarily for different purposes such as taking a shower, transportation, etc. Another feature is a new support system that can hold a standard Foley catheter more securely in place with the help of some new components, such as adaptors, added to them.

The new bladder catheter has two principal sections: a catheter that is inserted inside the bladder, and a lower tube that connects the catheter to the urine container. This two section construction allows the sections to be disconnected easily and also temporarily for different purposes such as taking a shower, transportation, etc. The catheter also has a valve or a three-way stopcock that will allow the person to close the opening of the catheter to prevent urine flow when the second section is disconnected. The three-way stopcock will also allow a selective irrigation of the catheter and the tubings, as well as obtaining a culture sample from the bladder with diminished chance of contamination. Another important feature of this unit is support system that it will be supported and held in place more securely, no longer like presently used Foley catheters that are allowed to wander around loosely and cause irritation and problems. A plastic compartment will be used to hold the upper and lower pieces together, also to have an alarm system to warn medical personnel if the lower tube is pulled out.

The Safe Catheter is made from latex or the same kind of materials as standard Foley catheters, and it comes in several sizes to match the size of the openings of the human urethras. One size, for example, is the length of an average man's urethra plus the length that goes inside the bladder and the length outside of the bladder. The catheter tip has side holes to allow urine to pass. When balloon 4 is inflated, it prevents the catheter from being pulled out of the bladder and also from irritating the surface of the bladder. The inflation port 12 has a one-way valve to allow injection to be made by a standard 5 to 10 ml syringe and to prevent the water from leaking out of the balloon after syringe removal.

Piece 5 is to prevent the rest of the outside of the catheter from slipping into the bladder. Between this flat piece and the opening of the penis an optional stretchable segment may be located. This segment can be made like a balloon that can be pulled and then return to its normal size later; it can also be made from stretchable piece of latex. This piece is to allow the catheter to be pulled some without the tip of the catheter being pulled out. This segment returns to its original length after the pulling has stopped. In this case the small tube for inflation of the balloon needs a longer length during pulling and will have a wavy length that straightens when the catheter stretches.

One or more soft doughnut-shaped balloons 14 may be inserted in the space between the tip of the penis and piece 5 to cushion the tip of the penis, and also to cover the length of the free part of the catheter to avoid looseness. These thin doughnut balloons will have a diameter of about 2.5 to 4 cm or so and one or more cm thickness or so. One part of their circumference will be open to allow this insertion over the catheter and then the circumference will be completed by using an adhesive tape over the circumference part of the balloon. In a point close to the end piece of this catheter there is a valve or three-way stopcock 6 that is used to shut the catheter closed. The three-way stopcock has the advantage of allowing selective irrigation of the catheter and outside tubing. With this method the irrigation of the upper piece can be done without fluid having to go through the lower tubing, and this will diminish the chance of infection. Also if the lower tube needs to be flushed, it does not have to go through the upper piece. This will also allow a culture sample to be selectively taken from the catheter without touching the lower tubing and will decrease the chance of contamination.. The valve and three-way stopcock (a catheter will have either valve or three-way stopcock), when closed, prevents free flow of the urine if lower tube 19 is removed.

The other embodiments of this new catheter beside FIG. 1 have a shield that stands around the penis like half of an egg shell shown in FIG. 2. This shield may be held in place by straps connected to its tips and sides that will hold it in place securely. A modified version of this unit may be used in female patients that is shorter and flatter in order to match the shape of the external female genitalia.

The embodiment of FIG. 7 is very similar to FIG. 1. The difference will be that this unit has two flat pieces, called H. pieces 216 and 217. These are made to allow the matching support system shown in FIG. 5 to be placed between these two H. pieces, and to prevent the catheter from moving back and forth.

The lower tube 19 is a latex tube that connects to the upper catheter part (Safe Catheter) that is inserted into the bladder. The tip end of tube 19 is shaped to match and fit the lower end of the Safe Catheter easily, like a male-female ends, so that after connection they will function as a continuous unit. This connection allows tube 19 to be disconnected if it is pulled hard. If a patient pulls the lower tube hard, it disconnects to prevent pulling of the tip of the catheter inside the bladder and possibly damaging the anatomy of the area. Furthermore this will allow the unit to be dismantled temporarily for certain purposes such as taking a shower, moving around, going some places, etc. It is important to keep in mind that sometimes or many times the Foley catheter is temporarily inserted only to allow the flow of urine in patients who cannot urinate because of stricture of the urethra or spasm in that area after certain operations or hypertrophy of the prostate, etc., or some other condition that prevents a patient from urinating. But such a condition does not necessarily need a urine collection bag.

The patient can open the valve or three-way stopcock to void the bladder through the Safe Catheter. This eliminates carrying a urine containing bag all the time, which is an unwanted and unnecessary discomfort, accompanied by some emotional feeling and misery. When the lower tube is connected, it continues to piece 22 in FIG. 1 (called Stabilizer piece) to which straps are connected for going around the waist and/or the thigh to prevent the lower tube from being left loose. Piece 22 also allows this unit to be inserted inside a matching plastic cradle. Tube 19 terminates with an end that will accept the tip of commonly used plastic bags for collection of urine. The length of the lower tube may vary from 15 to 45cm or so.

The plastic compartment is similar to a small case made from plastic or combination of plastic and a non-stretchable woven fabric. It has a molding inside in both surfaces of the lower and upper part that will be made from hard plastic; this molding is to accept and hold the different parts of the catheter so that they will be placed inside the moldings and be held safely. It has a door to shut closed to keep the pieces inside safely. The shape and size of the molding will vary to match with the unit that is to be used.

This plastic compartment performs one or more of the following functions:

1. To hold the connected ends of the Safe Catheter and tube 19 together.
2. To have a special molding to allow a standard Foley catheter to be held in place securely.
3. To have an alarm system that sounds if the tip of tube 19 is pulled out of the compartment.
4. Most importantly it will use different mechanisms to prevent the catheter from being pulled out of the bladder.

This plastic compartment is held in place by different ways as follows:

1. In some cases it is held by straps connected to its corners and sides that will go around the waist as well as one or both thighs to hold the plastic compartment sturdy, FIGS. 3 and 8.
2. In other cases it can be tightly attached or even to be part of the support system, for example, FIG. 3a. Or to be held on the support unit by straps going over the plastic compartment (not shown in Figures).

As mentioned earlier, one function of this piece is to allow the secure connection of the lower end of the Safe Catheter (and some other catheters) and the tip of the lower tube. Then the combination of these two pieces will be held in place securely inside a molding that will not allow the patient to pull them out. The moldings will have different configuration in different models. The plastic compartment will have a design to let the catheter that comes out of urethra of a patient to go through it and be held in place. When the lower end of the catheter is connected to the tip of the lower tube the whole unit and their connected parts will be placed and kept securely inside a matching cradle made for them. When these pieces are in place then a matching cover will go over them to hold the whole unit securely in place. An alarm system will also be part of this plastic compartment, that may be placed in the back of the door of the plastic compartment.

One such unit is shown in FIG. 4 and will be explained here in more details as an example. In this unit the plastic compartment 80 is made from a hard plastic and has a suitcase shape with a door that is opened prior to inserting the catheter inside it (this is not shown in this Figure). The molding inside this plastic compartment has surfaces, open spaces, and shapes to accept and hold the connected parts of the lower end of the Safe Catheter and tip of the lower tube and their related pieces such as the H. piece, the three-way stopcock and the tip of the inflation port of the balloon, etc., tight inside itself. The plastic compartment may have openings in its sides in front of these parts to allow them to be used without a need to open the plastic compartment (not shown in Figures). The plastic compartment may also have an alarm system as part of its construction. After these important pieces are in place then the door of this compartment (which also has matching moldings) and is made from hard plastic (or may have components of soft-plastic) will be closed, to hold those pieces in place safely.

If the lower tube is pulled hard, it will disconnect from the catheter. The small alarm system is made from presently available materials and techniques (possibly from a piece of piezoelectric connected to a watch battery). If a patient pulls the lower catheter out of its place in the compartment, the move will activate the alarm system to notify the nursing personnel. This alarm system shown in FIGS. 3–4 has an electric circuit that will be disrupted when the tip of the lower tube is in place. When the tip of tube 19 is pulled out and removed, then a spring 57 will push a piece of plastic 56 (shown in FIG. 4) to move forward and connect two metal ends (53 and its matching unmarked piece) of the electric circuit together by metal piece 54 to make the alarm sound. When the lower tube is to be placed, then button 51 is pressed in, to put the open part of plastic 56 in line with place for catheter's lower end so they can be connected. The surface of the plastic 56 may also be designed to close the tip of the lower end of the catheter after the tip of the lower tube is removed, to prevent dripping of urine.

These plastic compartment and its supportive straps all can be removed temporarily to allow patient to take a shower and walk around, etc., and also when the patient is no longer confused. A piece of plastic like a cap can cover the outside piece of Safe Catheter to prevent contamination during showering and also a piece of elastic in shape of half egg shell may go over the lower end to prevent the thighs and pants from touching and irritating the patient by moving the end of the catheter.

The Support System:

In order to prevent the catheter from being pulled out of the bladder, a support system holds the parts securely together. This system is made from different materials such as woven non-stretchable fabric that is tailored to stand on the pubic and genital area, and/or in some models to stand on the thigh or the thigh area as well as pubic area so that the unit will be kept secure to hold the catheter and related components securely in place. This system also has straps and a suspension mechanism that not only will hold the catheter securely inside the bladder but also it will prevent the lower tube from being free and wandering unprotected and uncomfortably. An upper pair of straps go around the waist to be tightened there; also a lower pair that go around the base of the thighs mostly one or it may use both of the thighs to hold the plastic compartment sturdy. The ends of these straps will be connected and tightened together by use of commonly used snaps. These snaps will be designed to be hard to be opened by patients, they may also be covered by a plastic cover and then to be taped, so that it will be very difficult for a patient to open it.

In cases where more caution is justified, this plastic compartment is part of a stronger system, and it is connected and held in place by a strong base unit. An example of such a base unit (here simply called pubic cover) is shown at 71 in FIG. 4, and it is kept in place in the pubic area by the straps 70, 72 connected to its corners. This pubic cover is made with a piece of woven non-stretchable synthetic fabric that may have parts made from hard plastic. Its corners are connected with straps 70 and 72. Alternatively this pubic cover may also be made from a non-stretchable screen (that can be a flexible metal) embedded inside a latex cover, or similar material or even fabric so that the surface of cover will be soft but the whole unit will be non-stretchable. This piece may also be further covered by a bubble-surfaced, thin, clear plastic or lining made from soft material such as cotton, to make its surface soft. A pad of absorbent material such as cotton may be used exchangeably since it has the advantage of absorbing drops of urine that may contaminate the area.

This pubic cover will start from pubic area and will continue to come toward penis as shown in FIG. 8 (its shape appears like the front of a narrow bikini) then it will narrow and be connected to a shield 76 that has a shape similar to a condom or half an egg shell. This shield is made from non-stretchable woven material covered by latex and may have components from hard plastic in order to give shape to its wall. Its inside and outside are covered by a soft cover to prevent discomfort and injury to the penis. The front wall of this shield can be opened to allow the catheter to be inserted inside it, and later to be closed (this is not shown in the Figures). The lower end of the shield has a hole to allow the catheter to go through it, and also it will be connected with plastic compartment 80.

The support system here referred as Male Support=M. Support may also include the plastic compartment as part of its own construction. This plastic compartment may have an alarm system similar to one mentioned earlier. This alarm system can be designed to be connected to a central alarming system. This plastic compartment will be held in place securely with use of straps.

This support system will be used to function in the following cases:

a. To hold the new catheter in place.

b. To hold standard Foley catheters in place with use of new adaptors.

c. To help in holding the lower tube in place.

A bag for collection of urine may be made to consist of two parts. This bag has a tube with an end piece that matches and connects to the lower end of tube 19. This tube is soft and made from latex and is held in place by straps and connected to the straps of the support system of the catheter. The tip of the tube of this bag has a valve that allows it to be closed to prevent leakage of the urine. This tubing will be easily bent so that it could be packed inside the outside cover bag. The sides of the plastic bag have a number of measurements of volume. This unit has a flat base to allow it be placed on the ground to stay sturdy. Also to have hangers to allow it to be hung from sides of the beds.

An outside cover unit for the bag will allow the plastic bag to be inserted in and out of the outside bag. It will have a zipper to allow the upper surface to open for this exchange. This unit to have straps inside to hold the tubing inside them easily. This unit is to prevent the person from feeling embarrassed by carrying a urine bag around. When needed, he can open the hand bag and pull the tip out and connect to the tip of the catheter and to open the valve of the catheter to empty bladder much simply. The container can be emptied in a convenient place. This will allow the unit to be used even inside a car.

I would like to mention that although there is a definite and profound difference between the external genitalia of the male and female patients, the units introduced here can be easily modified to allow both sexes to benefit from them. The difference in these units is that the cover for the penis will be replaced by a cover that will go over the external genitalia of the female patients and to be held in place tight with straps. And in the case of plastic compartment, in female patients this unit will stay over the cover that goes over the external genitalia and will be kept in place securely over it. And it may have some straps to go over the plastic compartment to keep it in place over the unit of female patients. Also the unit for males will be tilted to stand over one of the thighs; however in females it may be kept in center over the external genital area.

I claim:

1. A urinary catheter comprising walled catheter means comprising a proximal end portion and a distal tip end portion that is insertable through a person's urethra to place said distal tip end portion of said walled catheter means in a person's bladder while said proximal end portion of said walled catheter remains external to a person, said walled catheter means comprising passage means extending from said distal tip end portion for draining urine from a person's bladder to said proximal end portion of said walled catheter means, inflatable balloon means disposed on the outside of said walled catheter means proximate said distal tip end portion, an external inflation port and an inflation conduit extending from said inflation port to said balloon means for inflating said balloon means within a person's bladder so as to present an interference with a portion of a person's bladder at a person's urethra for resisting removal of the catheter from a person's bladder, said passage means comprising a port at said proximal end portion of said walled catheter means adapted to be connected to a flexible drain tube through which urine that has been drained through said passage means can be conveyed from the catheter, characterized in that said walled catheter means comprises between its distal tip end portion and its proximal end portion, a valve means comprising an internal valve disposed within said passage means and operated by an external actuator for selectively allowing and disallowing communication through said passage means between said port and said distal tip end portion, and characterized further in that said walled catheter means comprises plural catheter sections separably connected end-to-end at respective mating ends to form the catheter, one of said sections contains said distal tip end portion, said valve means, and one of said mating ends, and another of said sections contains the other of said mating ends and said proximal end portion.

2. A urinary catheter as set forth in claim 1 characterized further in that said one section comprises a port proximate said one mating end, and said valve means comprises a three-way stopcock for selectively communicating said distal tip end portion selectively to said one mating end of said one section and to said one section's port proximate said one mating end.

3. A urinary catheter as set forth in claim 2 characterized further in that said respective mating ends of said plural sections that are separably connected end-to-end are separably connected together by a connection that separates in response to application of a predetermined pulling force on said another section so that separation of said another section from said one section that occurs while said balloon means, when inflated to present an interference with a portion of a person's bladder at a person's urethra for resisting removal of the catheter from a person's bladder, remains in a person's bladder.

4. A urinary catheter as set forth in claim 3 characterized further in that one of said respective mating ends is telescopically disposed inside another of said mating ends, and yieldable holding means holds the telescopic engagement of said mating ends, but yields in response to such a predetermined pulling force, resulting in telescopic disengagement of said mating ends and hence separation of said another section from said one section.

5. A urinary catheter as set forth in claim 1 characterized further in that a signaling means is associated with said mating ends for giving a signal when said mating ends have been separated from each other.

6. A urinary catheter as set forth in claim 5 characterized further in that said signaling means comprises switch means disposed proximate said mating ends to sense when said mating ends of said plural sections have been separated from each other.

7. A urinary catheter as set forth in claim 6 characterized further in that a catheter holder having cradle means receives said mating ends of said plural sections in said cradle means, said switch means is disposed on said catheter holder, and strap means extends from said catheter holder for strapping said holder on a person.

8. A urinary catheter as set forth in claim 7 characterized further in that said strap means comprises waist strap means for going around a person's waist, said catheter further including thigh strap means engaged with said another section of said walled catheter means in spaced relation to said catheter holder for wrapping around a person's thigh to hold said another section of said walled catheter means on a thigh, and said catheter still further including suspension strap means extending from said waist strap means to said thigh strap means for preventing said thigh strap means from dropping.

9. A urinary catheter as set forth in claim 1 characterized further in that a catheter holder having cradle means receives said mating ends of said plural sections in said cradle means, and strap means extends from said catheter holder for strapping said holder on a person.

10. A Foley-type urinary catheter as set forth in claim 9 characterized further in that said strap means comprises waist strap means for going around a person's waist, said catheter further including thigh strap means engaged with said another section of said walled catheter means in spaced relation to said catheter holder for wrapping around a person's thigh to hold said another section of said walled catheter means on a thigh, and said catheter still further including suspension strap means extending from said waist strap means to said thigh strap means for preventing said thigh strap means from dropping.

11. A urinary catheter as set forth in claim 1 characterized further in that a further valve means is disposed on said one section to close said one of said mating ends when said other of said mating ends is disconnected from said one of said mating ends.

12. A urinary catheter as set forth in claim 1 characterized further in that said catheter comprises access-prevention means that is to be held on a person in covering relation to a person's external genitalia and to said one section of said catheter means so as to prevent a person from having manual access to that portion of said one section that is external to a person's external genitalia.

13. A urinary catheter as set forth in claim 1 characterized further in that a cup-shaped shell having a soft interior is disposed on the outside of said walled catheter means between said distal tip end portion and said valve means for fitting over the tip of a person's penis.

14. A urinary catheter as set forth in claim 1 characterized further in that a cup-shaped shell is disposed on the outside of said walled catheter means between said distal tip end portion and said valve means and has a rim for fitting against a person's body around a person's external genitalia to thereby enclose a person's external genitalia.

15. A urinary catheter comprising walled catheter means comprising a proximal end portion and a distal tip end portion that is insertable through a person's urethra to place said distal tip end portion of said walled catheter means in a person's bladder while said proximal end portion of said walled catheter remains external to a person, said walled catheter means comprising passage means extending from said distal tip end portion for draining urine from a person's bladder to said proximal end portion of said walled catheter means, inflatable balloon means disposed on the outside of said walled catheter means proximate said distal tip end portion, an external inflation port and an inflation conduit extending from said inflation port to said balloon means for inflating said balloon means within a person's bladder so as to present an interference with a portion of a person's bladder at a person's urethra for resisting removal of the catheter from a person's bladder, said passage means comprising a port at said proximal end portion of said walled catheter means adapted to be connected to a flexible drain tube through which urine that has been drained through said passage means can be conveyed from the catheter, characterized in that said walled catheter means comprises between its distal tip end portion and its proximal end portion, a valve means comprising an internal valve disposed within said passage means and operated by an external actuator for selectively allowing and disallowing communication through said passage means between said port and said distal tip end portion, and characterized further in that said valve means comprises a three-way stopcock.

16. A urinary catheter comprising walled catheter means comprising a proximal end portion and a distal tip end portion that is insertable through a person's urethra to place said distal tip end portion of said walled catheter means in a person's bladder while said proximal end portion of said walled catheter remains external to a person, said walled catheter means comprising passage means extending from said distal tip end portion for draining urine from a person's bladder to said proximal end portion of said walled catheter means, inflatable balloon means disposed on the outside of said walled catheter means proximate said distal tip end portion, an external inflation port and an inflation conduit extending from said inflation port to said balloon means for inflating said balloon means within a person's bladder so as to present an interference with a portion of a person's bladder at a person's urethra for resisting removal of the catheter from a person's bladder, said passage means comprising a port at said proximal end portion of said walled catheter means adapted to be connected to a flexible drain tube through which urine that has been drained through said passage means can be conveyed from the catheter, characterized in that said walled catheter means comprises between its distal tip end portion and its proximal end portion, plural sections separably connected end-to-end at respective mating ends to form the catheter, one of said sections contains said distal tip end portion and one of said mating ends, and another of said sections contains the other of said mating ends and said proximal end portion, and characterized further in that a valve means is disposed on said one section to close said one of said mating ends when said other of said mating ends has been separated from said one of said mating ends.

17. A urinary catheter comprising walled catheter means comprising a proximal end portion and a distal tip end portion that is insertable through a person's urethra to place said distal tip end portion of said walled catheter means in a person's bladder while said proximal end portion of said walled catheter remains external to a person, said walled catheter means comprising passage means extending from said distal tip end portion for draining urine from a person's bladder to said proximal end portion of said walled catheter means, inflatable balloon means disposed on the outside of said walled catheter means proximate said distal tip end portion, an external inflation port and an inflation conduit extending from said inflation port to said balloon means for inflating said balloon means within a person's bladder so as to present an interference with a portion of a person's bladder at a person's urethra for resisting removal of the catheter from a person's bladder, said passage means comprising a port at said proximal end portion of said walled catheter means adapted to be connected to a flexible drain tube through which urine that has been drained through said passage means can be conveyed from the catheter, characterized in that said walled catheter means comprises between its distal tip end portion and its proximal end portion, plural sections separably connected end-to-end at respective mating ends to form the catheter, one of said sections contains said distal tip end portion and one of said mating ends, and another of said sections contains the other of said mating ends and said proximal end portion, and characterized further in that said one section comprises a port proximate said one mating end, a three-way stopcock having an external actuator is disposed in said one section proximate said respective mating ends for selectively communicating said distal tip end portion selectively to said one mating end of said one section and to said one section's port proximate said one mating end.

18. A urinary catheter comprising walled catheter means comprising a proximal end portion and a distal tip end portion that is insertable through a person's urethra to place said distal tip end portion of said walled catheter means in a person's bladder while said proximal end portion of said walled catheter remains external to a person, said walled catheter means comprising passage means extending from said distal tip end portion for draining urine from a person's bladder to said proximal end portion of said walled catheter means, inflatable balloon means disposed on the outside of said walled catheter means proximate said distal tip end portion, an external inflation port and an inflation conduit extending from said inflation port to said balloon means for inflating said balloon means within a person's bladder so as to present an interference with a portion of a person's bladder at a person's urethra for resisting removal of the catheter from a person's bladder, said passage means comprising a port at said proximal end portion of said walled catheter means adapted to be connected to a flexible drain tube through which urine that has been drained through said passage means can be conveyed from the catheter, characterized in that said walled catheter means comprises between its distal tip end portion and its proximal end portion, plural sections separably connected end-to-end at respective mating ends to form the catheter, one of said sections contains said distal tip end portion and one of said mating ends, and another of said sections contains the other of said mating ends and said proximal end portion, and characterized further in that a catheter holder is attached to a person and contains said respective mating ends, and in that access-prevention means is held on a person in covering relation to a person's external genitalia and to said one section of said catheter means so as to prevent a person from having manual access to that portion of said one section that is external to a person's external genitalia.

19. A urinary catheter comprising walled catheter means comprising a proximal end portion and a distal tip end portion that is insertable through a person's urethra to place said distal tip end portion of said walled catheter means in a person's bladder while said proximal end portion of said walled catheter remains external to a person, said walled catheter means comprising passage means extending from said distal tip end portion for draining urine from a person's bladder to said proximal end portion of said walled catheter means, inflatable balloon means disposed on the outside of said walled catheter means proximate said distal tip end portion, an external inflation port and an inflation conduit extending from said inflation port to said balloon means for inflating said balloon means within a person's bladder so as to present an interference with a portion of a person's bladder at a person's urethra for resisting removal of the catheter from a person's bladder, said passage means comprising a port at said proximal end portion of said walled catheter means adapted to be connected to a flexible drain tube through which urine that has been drained through said passage means can be conveyed from the catheter, characterized in that said walled catheter means is removably received in a catheter holder adapted to be secured in place externally on a person, and said catheter holder contains a signaling means that gives a signal in response to attempted removal of the catheter from a person's bladder by pulling on an external portion of the catheter.

20. A urinary catheter as set forth in claim 19 characterized further in that said catheter holder comprises a tortuous channel within which a portion of said walled catheter means is disposed and said signaling means is organized and arranged such that an attempted removal of the catheter from a person's bladder by pulling it through said tortuous channel is prevented and results in said signaling means giving a signal indicative of such attempted removal.

21. A urinary catheter as set forth in claim 19 characterized further in that said walled catheter means comprises plural catheter sections separably connected end-to-end at respective mating ends to form the catheter, one of said sections contains said distal tip end portion and one of said mating ends, and another of said sections contains the other of said mating ends and said proximal end portion, and in that said signaling means is organized and arranged to give a signal when said other of said mating ends is disconnected from said one of said mating ends, and a valve means is disposed on said one section to close said one of said mating ends when said other of said mating ends is disconnected from said one of said mating ends.

* * * * *